US011350677B2

(12) United States Patent
Shekhani et al.

(10) Patent No.: US 11,350,677 B2
(45) Date of Patent: Jun. 7, 2022

(54) SYSTEM AND METHOD FOR INFANT SWADDLE TRANSITION AND ALTERNATIVE

(71) Applicant: TWO BABY BEARS AND CO. LLC, Ballwin, MO (US)

(72) Inventors: Ummekulsoom Shekhani, Ballwin, MO (US); Husain Shekhani, Ballwin, MO (US)

(73) Assignee: Two Baby Bears and Co. LLC, Ballwin, MO (US)

( * ) Notice: Subject to any disclaimer, the term of this patent is extended or adjusted under 35 U.S.C. 154(b) by 0 days.

(21) Appl. No.: 16/577,448

(22) Filed: Sep. 20, 2019

(65) Prior Publication Data

US 2020/0093189 A1    Mar. 26, 2020

Related U.S. Application Data

(60) Provisional application No. 62/733,637, filed on Sep. 20, 2018.

(51) Int. Cl.
*A41B 13/06* (2006.01)
*A61F 5/37* (2006.01)
*A61F 5/05* (2006.01)

(52) U.S. Cl.
CPC ............... *A41B 13/06* (2013.01); *A61F 5/05* (2013.01); *A61F 5/37* (2013.01); *A61F 5/373* (2013.01)

(58) Field of Classification Search
CPC . A41B 13/06; A61F 5/05; A61F 5/058; A61F 5/05825; A61F 5/05841; A61F 5/05858; A61F 5/37; A61F 5/3715; A61F 5/3723; A61F 5/373; A61F 5/05833

USPC ........................................................ 128/870
See application file for complete search history.

(56) References Cited

U.S. PATENT DOCUMENTS

| 5,618,263 | A  | * | 4/1997  | Alivizatos ........... A61F 5/05841 128/878 |
| 6,322,462 | B1 | * | 11/2001 | Kafer ................. A63B 69/0002 128/878 |
| 7,954,187 | B1 |   | 6/2011  | Earnest |
| 8,375,486 | B2 |   | 2/2013  | Earnest |
| 9,060,549 | B2 |   | 6/2015  | Buckson |
| 9,179,711 | B2 |   | 11/2015 | Krawchuk |
| 9,572,376 | B2 | * | 2/2017  | Gangan ................. A41B 13/06 |
| 2004/0149293 | A1 | * | 8/2004 | Freedman ............... A61F 5/373 128/878 |

(Continued)

FOREIGN PATENT DOCUMENTS

WO    WO-2018141983 A1 *    8/2018    ............... A61F 7/02

*Primary Examiner* — Keri J Nelson
(74) *Attorney, Agent, or Firm* — Polsinelli PC (57) ABSTRACT

The disclosure provides infant swaddling device or system in the form of two sleeves to help dampen the moro reflex—one for each arm—with the option of a non-flexible backing (or splint) and weighting. This device safely mimics the swaddling effect by adequately reducing the moro (twitching) reflex and flailing of arms, thus helping baby sleep for longer periods of time. The infant swaddle device may eliminate or reduce the risk of suffocation or overheating that other swaddle transition suits, garments, methods, or devices pose. This device can be used as a swaddle alternative; in conjunction of a swaddle blanket or sack, pod, etc. or without; or as a transition device to easily wean infants from the swaddle.

14 Claims, 6 Drawing Sheets

(56) References Cited

U.S. PATENT DOCUMENTS

| | | |
|---|---|---|
| 2011/0180079 A1 | 7/2011 | Krawchuk |
| 2011/0191932 A1 | 8/2011 | Earnest |
| 2013/0283527 A1 | 10/2013 | Houston et al. |
| 2015/0000036 A1 | 1/2015 | Krawchuk |
| 2016/0128392 A1 | 5/2016 | Krawchuk |
| 2016/0362024 A1 | 12/2016 | Simon et al. |
| 2018/0014987 A1* | 1/2018 | Karabel ................. A61F 13/10 |
| 2018/0168240 A1 | 6/2018 | Parker |

* cited by examiner

SYSTEM AND METHOD FOR INFANT SWADDLE TRANSITION AND ALTERNATIVE

CROSS REFERENCE TO RELATED APPLICATIONS

This application claims priority to U.S. Provisional Application No. 62/733,637, filed Sep. 20, 2018, the contents of which are entirely incorporated by reference herein.

FIELD

The present subject matter relates to infant sleepwear, specifically swaddle accessories and devices for safe and healthy infant sleep.

BACKGROUND

Current infant sleep safety guidelines released by the AAP (American Academy of Pediatrics) state that infants should be placed on their backs to sleep in a crib free of blankets, bumpers, plush toys, and other items. Ideally, the guidelines state that babies should share a room with their parents for the first six months to a year of their lives, use a pacifier as a sleep aid, and have a fan for circulating air in the room to help reduce the risk of SIDS (Sudden Infant Death Syndrome). Studies show that the campaigns promoting recent guidelines has in fact reduced the occurrence of SIDS significantly within the last few decades.

However, it has been shown that many infants dislike sleeping on their backs and would much rather sleep more comfortably on their sides or stomach. The cause isn't exactly known, but it is speculated that this may be because of the baby's positioning in the womb, or because of the way humans have evolved over generations, or simply because babies prefer the feeling of snugness that the side laying or belly-down positions provide. This dilemma has been solved by the time-tested practice of swaddling.

Swaddling is the art of wrapping a baby snugly in a blanket (or similar material) with arms straight at their sides so that their extremities are controlled and restricted in movement. To swaddle an infant safely and satisfactorily, one must make sure that the infant's arms are properly immobilized but that the legs and hips are still given some access to horizontal and vertical movement. Swaddling provides babies with the snug, close-fitting environment newborns need and mimics womb-like sensations, and thus inhibits the moro (startle) reflex. Usually, if a baby is not swaddled or swaddled incorrectly, this innate sudden jerking movement or twitching of the arms startles the baby awake repeatedly, leading to little or poor quality sleep for the infant and parents, which is not sustainable in the long term for either party's mental or physical health and well-being.

Although it seems simple in theory, swaddling a baby correctly is something many parents struggle with. Parents not only need to worry about making sure that they have swaddled their baby tightly enough so that the arms can't escape and therefore loosen and unravel the swaddle, but they also have to make sure that the swaddle is not too tight around the hips, legs, and chest, thus affecting breathability or risking hip dysplasia; or swaddling the infant in a blanket or fabric that does not provide proper ventilation and cause baby to overheat. In addition to the above, many parents aren't familiar with different swaddling techniques and end up prematurely discarding the swaddle and its numerous benefits because the baby continuously wriggles free of the confines of the swaddle. This presents another significant problem: the fabric of the swaddle covering the neck and face of the infant and presenting a suffocation hazard. For younger babies, this is not too much of a risk, as they usually do not yet have the strength to break their arms out of the swaddle, but as the baby reaches one month of age, this lack of ability to properly swaddle ends up compromising the same rules that were put in place by the AAP to reduce the number of SIDS related deaths.

Because of the difficulties mentioned above, many caregivers initially try to swaddle their baby for the first several weeks, but then are quickly forced to abandon the practice and incorrectly believe that their baby just does not like being swaddled, or that their baby is a swaddle "Houdini," and simply cannot be soothed using the age-old, time-tested formula.

To combat the numerous issues mentioned above in regards to the difficulties in being able to swaddle an infant properly, safely, and effectively, different solutions have been devised and are found in the current retail market—solutions such as swaddle pods, swaddle sacks, swaddle straps, and weighted sleep suits (some zippered and some secured with a hook and loop mechanism), which replace the conventional blanket swaddle. All of these swaddle garments solve one or more of the difficulties that were cited earlier, but simultaneously present other substantial risks or issues (such as overheating, suffocation hazard due to Velcro closure, more freedom of movement for arms, etc.). Due to SIDS concerns, infants are required to be out of the swaddle once they start rolling over in order to prevent suffocation. All of the swaddles available on the market focus on transitioning the infant out of the swaddle by either taking one arm out at a time, or by completely removing the suit due to concerns of rolling over and suffocating, thus leaving the baby bereft of the security they've developed over months through the sleep association respective sleep garment. Although there are several transitional products available on the market, they either give the baby an elevated amount of freedom to move their limbs or may present potential overheating concerns.

Thus, tt would be advantageous to have a swaddle transition device that overcomes the problem of completely eliminating the infant's sleep association that has been established through months of diligent daily swaddle use while also staying true to SIDS prevention guidelines.

Further, there is also a need for a swaddling device that helps to keep the infant's arms down at their sides without causing an overheating concern due to copious amounts of fabric—a device or accessory that can be used with or without a swaddle garment.

Therefore, there is a necessity for an infant swaddle device that addresses the interests and complications cited above, as explained and declared in the succeeding drawings and description. It is an aim of this invention to offer a novel or alternative swaddling device or accessory that restrains an infant's arms through the use of sleeves to be used in multiple settings and methods.

BRIEF SUMMARY

Described herein is an infant swaddle device. The infant swaddle device includes a sleeve having an inside facing portion and an outside facing portion, the inside facing portion and the outside facing portion each having an attachment mechanism. The sleeve is operable to be wrapped around an infant's arm such that the infant's elbow is positioned within the sleeve. The elbow and sleeve may be restrained from bending or may be able to bend when the sleeve is in position. The sleeve reduces the startle reflexes of the infant when wrapped around the infant's arm while the infant is sleeping.

In an aspect, when the sleeve is wrapped around the infant's arm, the inside facing portion and the outside facing portion are reversibly attached together with the attachment mechanisms. For example, the attachment mechanisms may include, but are not limited to hook and loop fasteners, buttons, zippers, or snaps. In an aspect, an upper edge of the sleeve is operable to rest just below the infant's armpit, and a bottom edge of the sleeve is operable to rest just above the infant's wrist or just under the infant's elbow when the sleeve is wrapped and secured around the infant's arm.

In some aspects, the sleeve further comprises one or more chambers inside the sleeve operable to hold a weighting and/or one or more splints. The weighting may include, but is not limited to at least one of a natural or synthetic material, sand, beads, and fabric. In some aspects, the one or more splints may extend the width of the sleeve to reduce or prevent the infant's elbow from bending when the sleeve is wrapped around the infant's arm. The splint may include plastic, metal, and/or cardboard, and may be surrounded and covered by a foam or cloth backing.

In an aspect, the sleeve further includes a tab extending from a longitudinal side of the sleeve near one end of the sleeve. The tab may have a securing mechanism for connecting the sleeve to a second sleeve for storage. In another aspect, the inside facing portion of the sleeve may further include one or more anti-slip mechanisms operable to contact the infant's arm and reduce movement of the sleeve. The one or more anti-slip mechanisms may include silicone, such as medical-grade silicone.

Further provided herein is an infant swaddle system with two infant swaddle devices, each intended to be wrapped around each of the infant's arms. Each sleeve may further include a tab extending from a longitudinal side of the sleeve near one end of the sleeve with a securing mechanism for connecting the two infant swaddle devices together for storage.

Also provided herein is a method of reducing the startle reflexes of an infant. The method may include wrapping a sleeve of an infant swaddle device around the infant's arm such that the infant's elbow is positioned within the sleeve. The sleeve and elbow may be restrained from bending or may be able to bend when the sleeve is in position. The method may further include wrapping a second sleeve around the infant's other arm. In various aspects, the infant may be swaddled or unswaddled.

Beyond what is mentioned above, further implementations, advantages, and original features will be explained in the detailed description and drawings that follow.

BRIEF DESCRIPTION OF THE DRAWINGS

The drawings provided herein illustrate two or more realizations of the aforementioned concept, by way of example only, and not by its limitations.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout the above disclosure will now be presented. The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape or other word that substantially modifies, such that the component need not be exact. For example, "substantially rectangular" means that the object resembles a rectangle, but can have one or more deviations from a true rectangle. The terms "comprising," "including" and "having" are used interchangeably in this disclosure. The terms "comprising," "including" and "having" mean to include, but not necessarily be limited to the things so described.

Many infants do not respond well to the transitioning swaddles that are currently available and protest the arms being abruptly unrestrained by not sleeping as well or for as long as normal. Also, as the infant reaches the age (usually around six months) during which the swaddle becomes unnecessary but is still used as a sleep crutch and association, parents may desire to move the baby away from the swaddle but in a gentle, coaxing manner, one that does not disrupt the successful routine and sleep patterns already in place.

Provided herein is a swaddle device for infants operable to provide a secure, restrained environment to encourage an infant's arms to stay in a downward position, thus inhibiting the moro reflex. The swaddle device described herein may be safely and successfully used with an existing swaddle garment, without a swaddle garment, or be used as a transition device for older babies. For example, the swaddle device may promote safety and ease in current swaddling practices and techniques, with or without the use of a traditional swaddle.

The present swaddle device provides an alternative to the traditional infant swaddle in the form of sleeves. An advantage of the present swaddle device is that it can help to easily transition the infant out of the swaddle or be used as a swaddle alternative for those babies who don't prefer to be traditionally swaddled but still have a strong startle reflex. It fulfills the function of a swaddle, but with a minimalistic approach. Other advantages include that it does not present the suffocation risk due to the arms being properly and separately restrained, and there is no risk of overheating, since the fabric used in this device is minimal, breathable, and not bulky, and also does not cover the infant's whole body from neck to toe. Another advantage is that the risk of hip dysplasia or improper management of the tightening of the limbs and torso with this swaddle device (in an attempt to get a tighter swaddle) is nil due to its design and implementation relating only to the infant's arms. Another advantage of the swaddle device is that it gives parents or caregivers the option of using swaddle blankets without worrying about their babies' arms escaping; it also helps parents use the other swaddle garments properly. Another advantage is that the swaddle device can be used from the newborn stage until the baby is transitioning out of the swaddle, and it can be used for older babies who are stronger as the weighting in the device can be adjustable. Another advantage is that when the infant is ready to be unswaddled, the sleeves may function as a buffer to simply restrain the arms while the rest of the body can be unconstrained.

The swaddle device provided herein relates generally to a swaddle device that restrains the arms of infants to their sides without restricting the chest, back, or any other part of the torso. In some examples, the swaddle device may use added weight to promote ease and comfort in sleeping. In other examples, the swaddle device may be an alternative baby swaddle device or accessory that is configured to act as a swaddle transitioning device or alternative. It may mimic the traditional swaddle by restraining the infant's arms in the form of two sleeves, one for each arm, without restraining the infant's legs or torso. Without being limited to a particular theory, the swaddle device may be a safer, simpler, more effective way of swaddling a baby than the swaddle garments currently in retail and can be used in conjunction with or without a swaddle garment or in the car seat and stroller. The effectiveness of the swaddle device is not limited to just one arrangement. For example, the swaddle device may be configured to provide security and comfort to the infant in order to reduce the reflexive flailing (moro reflex) and habitual waking patterns that dominate their sleep cycles.

As generally seen in FIGS. 1A-6, the infant swaddle device includes a sleeve 10 having an inside facing portion and an outside facing portion. The inside facing portion is configured to face towards the infant's arm and the outside facing portion is opposite the inside facing portion and is configured to face away from the infant's arm as the sleeve is wrapped around the infant's arm. The sleeve may be made of a single piece of fabric or multiple layers of fabric. In some examples, the sleeve may include 2, 3, 4, 5, or 6 layers of fabric. In at least one example, the sleeve includes 4 layers of fabric.

Figure 1A:
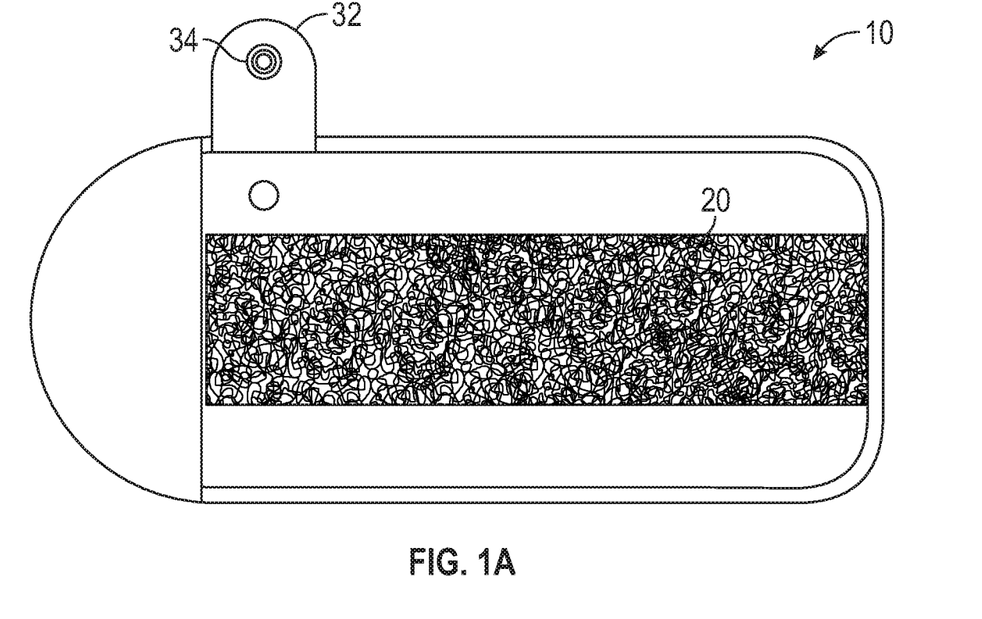
FIG. 1A is a view of the inside facing portion of the swaddle device with one tapered end, in one example.
Figure 1B:
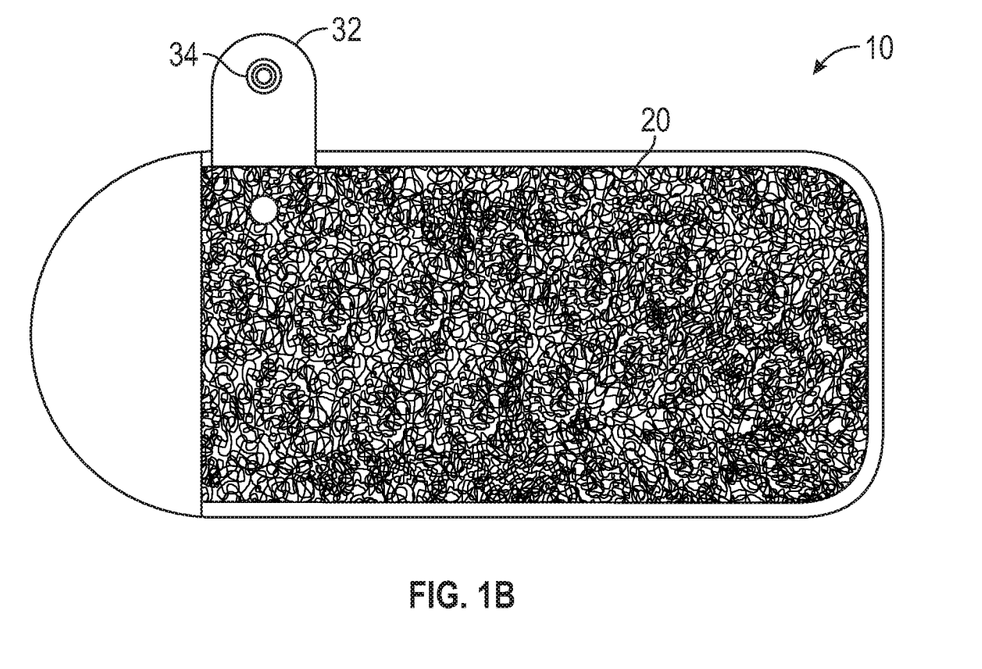
FIG. 1B is a view of the inside facing portion of the swaddle device with one tapered end, in one example.
Figure 1C:
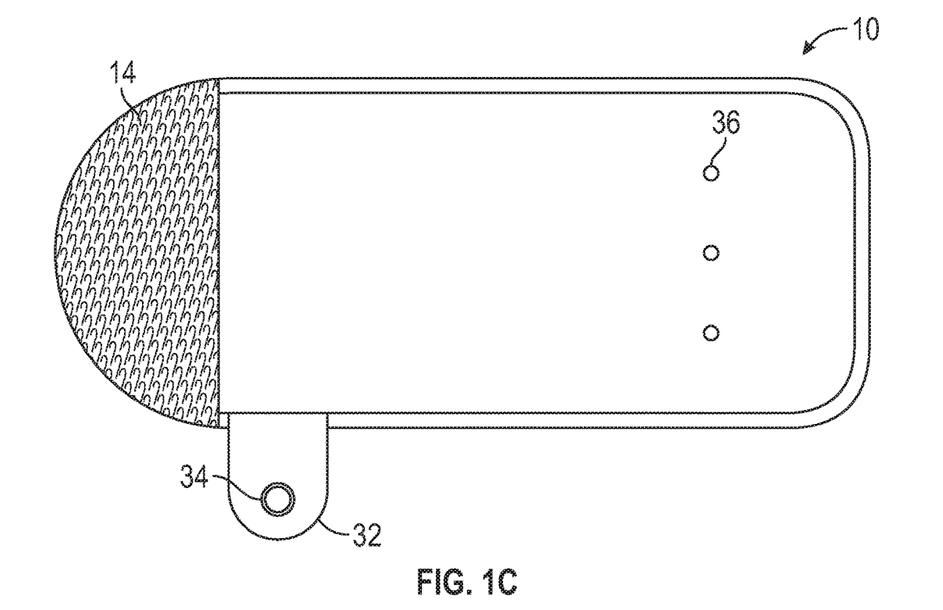
FIG. 1C is a view of the outside facing portion of the swaddle device with one tapered end, in one example.
Figure 3:
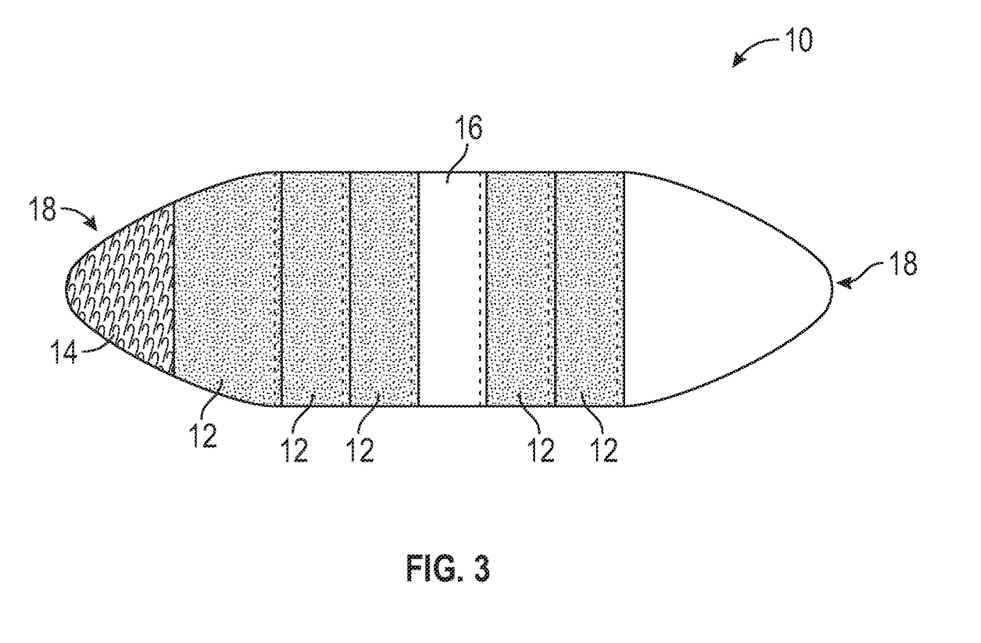
FIG. 3 is a view of the inside facing portion of the swaddle device with two tapered ends and pockets, in one example.
Figure 4:
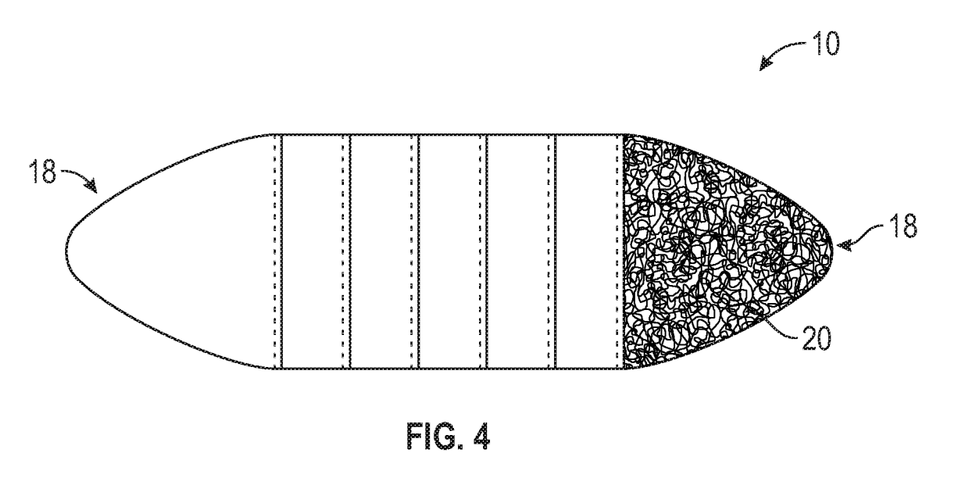
FIG. 4 is a view of the outside facing portion of the swaddle device with two tapered ends and pockets, in one example.
Figure 5:
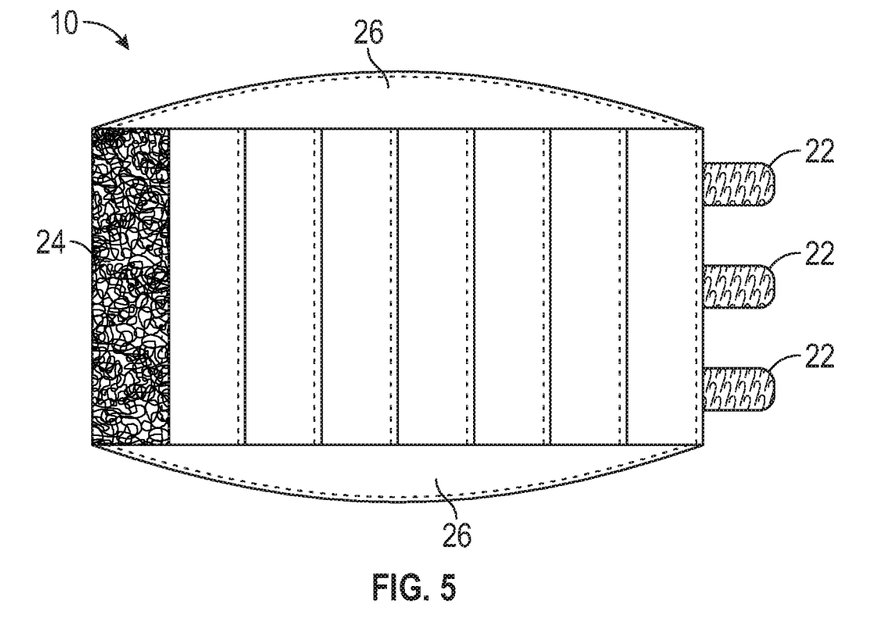
FIG. 5 is a view of the outside facing portion of the swaddle device with one tapered end and pockets, in one example.
Figure 6:
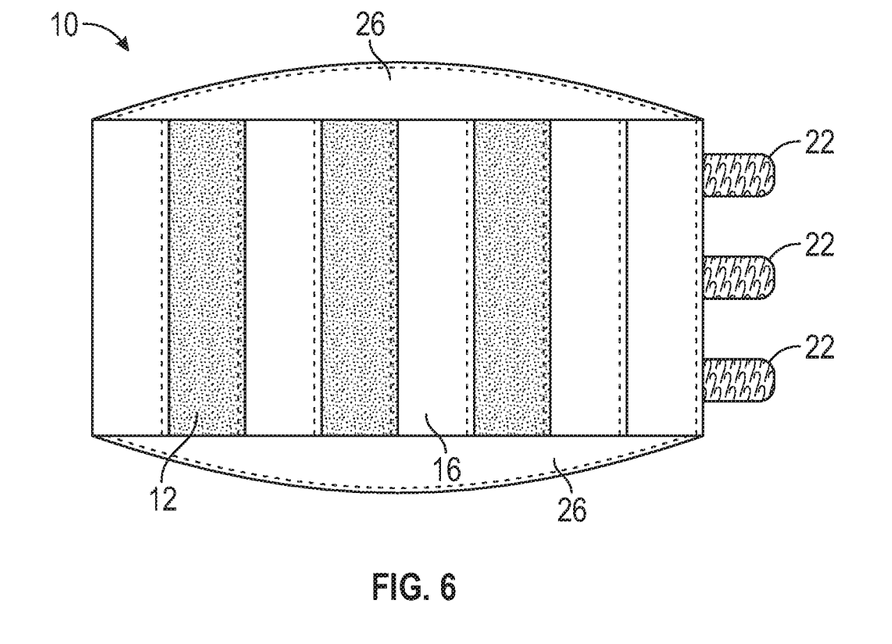
FIG. 6 is a view of the inside facing portion of the swaddle device with one tapered end and pockets, in one example.

The sleeve may be substantially rectangular with two parallel longitudinal sides and two end sides between the longitudinal sides. The ends may be substantially flat, rounded, or tapered ends. In an embodiment, the sleeve may include one tapered end and one substantially flat end, as seen in FIGS. 1A-1C. In some examples, the tapered end may be composed of multiple straps 22, for example as seen in FIGS. 5-6. The tapered end may include the attachment mechanism on the inside facing portion. In another embodiment, the sleeve may include tapered ends on both ends, as seen in FIGS. 2A-2C and 3-4. This may allow the attachment mechanisms to join together around the infant's elbow. In other examples, the longitudinal sides may further include a rounded portion 26, as seen in FIGS. 5-6.

The length of the sleeve may range from up to about 20 cm to about 40 cm. In some examples, the sleeve may have a length of about 25 cm when it has only one tapered end and may have a length of about 36 cm when it has two tapered ends. The width of the sleeve may range from up to about 5 cm to about 15 cm. In some examples, the width of the sleeve may be about 10.8 cm.

Figure 7A:
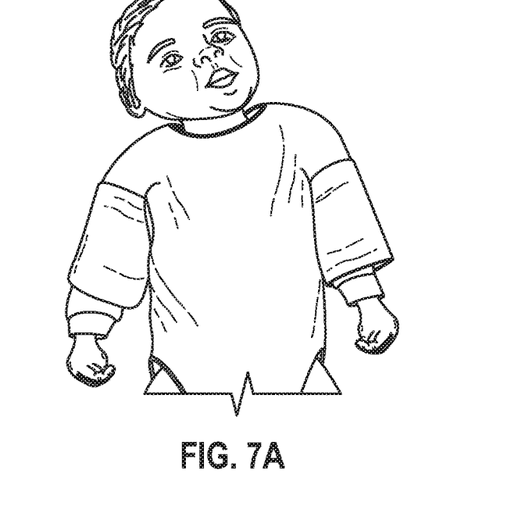
FIG. 7A is an illustration two sleeves when secured and wrapped around an infant's arms and connected using the attachment mechanisms, in one example.
Figure 7B:
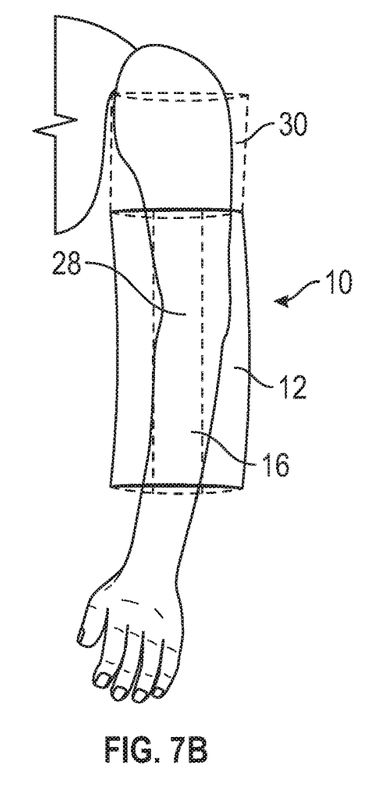
FIG. 7B is an illustration the sleeve when it is secured and wrapped around an infant's arm and connected using the attachment mechanisms, in one example.

The sleeve is operable to be placed and wrapped around the infant's arm such that the infant's elbow is positioned within the sleeve, as seen in FIGS. 7A and 7B. In some examples, the sleeve and elbow may be restrained from bending when the sleeve is in position. In other examples, the sleeve and elbow may bend when the sleeve is in position. Wrapping and securing the sleeve with the attachment mechanisms allows the sleeve to reduce moro/startle reflexes of the infant while the infant is sleeping. For example, an upper edge of the sleeve is operable to rest just below the infant's armpit and a bottom edge of the sleeve is operable to rest just above the infant's wrist or just under the infant's elbow.

The inside facing portion and the outside facing portion of the sleeve each may include an attachment mechanism 14, 20 such that the attachment mechanisms attach or connect together when the sleeve is wrapped around an infant's arm. When the sleeve is wrapped around the infant's arm, the inside facing portion and the outside facing portion are reversibly attached together with the attachment mechanisms. The attachment mechanisms may include but are not limited to hook and loop fasteners, buttons, zippers, snaps, or any mechanism capable of securing the sleeve around the infant's arm. In some examples, the attachment mechanism may be a loop and hook mechanism at selected points on the sleeve to easily connect around the infant's arm in a snug and tight-fitting manner.

Figure 2A:
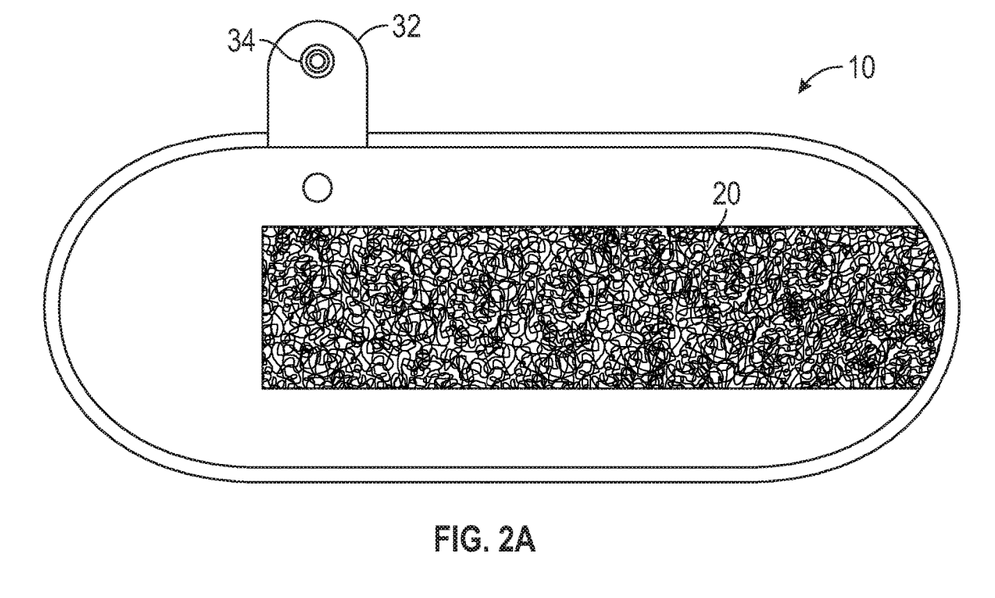
FIG. 2A is a view of the inside facing portion of the swaddle device with two tapered ends, in one example.
Figure 2B:
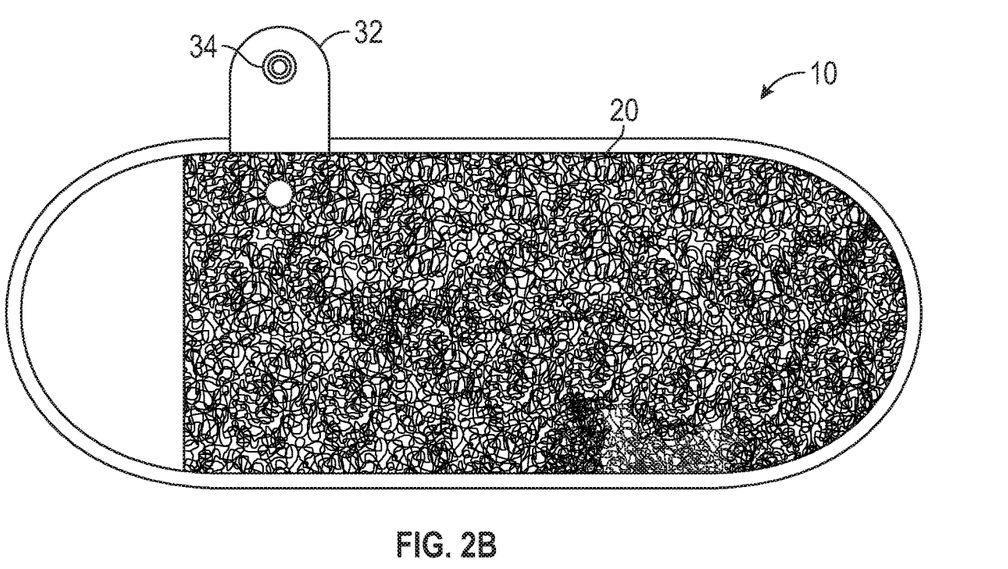
FIG. 2B is a view of the inside facing portion of the swaddle device with two tapered ends, in one example.

As seen in FIGS. 1A, 1B, 2A, and 2B, the outside facing portion may include loop fasteners along a length in the center of the sleeve. In some examples, the loop fasteners 20 may extend from a first end on the outside facing portion of the sleeve to a point past the midpoint of the sleeve but not reaching the second end of the outside facing portion. The length of the loop fasteners may range from about 15 cm to about 32 cm, depending on if the sleeve has one or two tapered ends. For example, the length of the loop fasteners may be about 10.5 cm long when the sleeve has one tapered end and be about 30.5 cm long when the sleeve has two tapered ends. In additional examples, the loop fasteners 20 may be in a strip and not extend the full width of the sleeve, as seen in FIGS. 1A and 2A. For example, the loop fasteners may have a width of about 5 cm. In other examples, the loop fasteners 20 may extend the full width of the sleeve, as seen in FIGS. 1B and 2B.

Figure 2C:
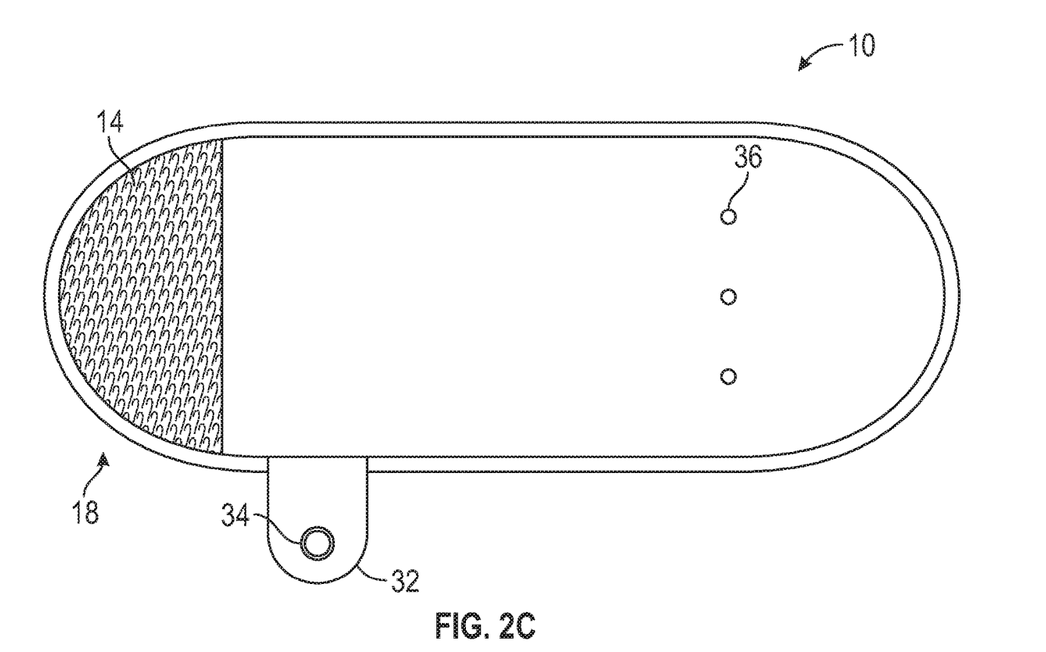
FIG. 2C is a view of the outside facing portion of the swaddle device with two tapered ends, in one example.

As seen in FIGS. 1C and 2C, the inside facing portion may include hook fasteners 14 at a tapered end 18 of the sleeve. For example, the hook fasteners 14 are located at the end without loop fasteners 20 on the corresponding outside facing portion. The section of the hook fasteners may have a length of about 5 cm and may cover the full width of the sleeve. In some examples, each strap 22 at the tapered end may include hook fasteners, as seen in FIGS. 5 and 6. In another example, the attachment mechanism may be a button and an elastic looping mechanism at selected points on the sleeve to easily connect around the infant's arm in a snug and tight-fitting manner.

The inside facing portion of the sleeve may further include one or more anti-slip mechanisms operable to contact the infant's arm and reduce movement of the sleeve. In some examples, the one or more anti-slip mechanisms may include silicone. As seen in FIGS. 1C and 2C, the anti-slip mechanisms 36 may be medical-grade silicone dots arranged near the end of the inside facing portion of the sleeve, opposite the attachment mechanism. The inside facing portion of the sleeve may include 1, 2, 3, 4, 5, or 6 anti-slip mechanisms.

In some embodiments, the swaddle device may include a removable, non-flexible straight backing (splints) 16 in the sleeves helps to keep the infant's elbow from bending and reaching the face, thereby waking up the baby and interrupting an otherwise peaceful slumber. The splint may be made of plastic, metal, and/or cardboard. In some examples, the splint may be surrounded and covered by a foam or cloth backing. The splint may also make it difficult for the infant to accidentally take his pacifier out of the mouth. Pacifier use is recommended by the AAP to reduce the likelihood of SIDS. In some examples, the swaddle device may be used without splints, as the sleeve itself may provide sufficient restriction of the movement of the infant's elbow.

In some embodiments, the sleeves of the swaddle device may further include weighting. The weighting in the sleeves may further encourage the feeling of security for infants. Weighted sections of the sleeves extend gentle pressure on the infant's arms and help to keep their arms lowered as is recommended for swaddling in the supine position. This way, when the neurological reflexive twitching occurs while the infant is sleeping, he is able to stay asleep and not wake up prematurely. The weighting may be accomplished by changing the thickness of the sleeve, the amount of fabric, and/or material used for weighting. In various examples, the weighting may be weighted material that is safe for use in children's clothing products, such as, but not limited to: polyfill fiber or pellets, glass beads, sand, bamboo beads, weighty fabric, or any other item that is acceptable for this purpose. In some examples, the weighting may be placed between two layers of fabric in the sleeve. In at least one example, the sleeve has four layers, with glass beads encased within the middle two layers. In some examples, the amount of weighting is adjustable, such that the appropriate amount of weighting may be used for the size or weight of the infant. For example, weighting may be added as the infant grows and becomes stronger. The weight of the weighting may range from about 3 oz to about 6 oz.

The sleeves may include one or more closed or closeable chambers inside the sleeve operable to hold the weighting and/or the splint. In some examples, the splint and weighting may be removable from the chambers. As seen in FIGS. 3 and 4, the sleeves may include several rectangular pockets or chambers 12 for the weighting and/or splints to be distributed throughout. In some examples, the chambers may be square, such as a 1 in by 1 in square or a 2 in by 2 in square. In one example, as seen in FIG. 6, the swaddle device includes sections or chambers where there is an alternation of splints and weighted parts, one after the other, so that the weighting and splints are evenly distributed throughout the sleeve. In another example, the splint may be contained only in one chamber (to be placed under the elbow) and the weighting may be evenly distributed in chambers throughout the sleeve in order to minimize the excessive material and to promote breathability and a lightweight design. For example, as seen in FIG. 3, the splint 16, or straight backing, which may be removable, may be placed in the middle chamber. In another example, the weighting may be contained in only the anterior or posterior portion of the device. In another embodiment, the splint and weighted sections may be covered with a lightweight fabric on the inside and the outside of the sleeve, providing a comfortable backing on the infant's arm. Thus, the chambers may be fully covered by additional fabric and not be visible externally.

The swaddle device may also be made and still be fully functional without the use of splint(s). If no splint is used, the amount of weighting may be increased and the sleeve in order to continue to suppress the baby's moro reflex while still allowing for a slight increase in movement of the infant's arms, thus maximizing on comfort.

In an embodiment, the sleeve of the swaddle device may further include a tab 32 extending from a longitudinal side of the sleeve near one end of the sleeve, as seen in FIGS. 1A-2C. The tab 32 may have a securing mechanism 34 for connecting the sleeve to a second sleeve for storage or for ease of finding. For example, the two sleeves 10 may be compactly rolled up and then secured to each other using the securing mechanism to function in one unit. The securing mechanism may also be used to fold over the tab when not needed, as the outside facing portion of the sleeve may include a complimentary portion of the securing mechanism. For example, when the sleeves are in use and wrapped around the infant's arm, the tab may be folded down and the securing mechanism may be secured to itself. Non-limiting examples of the securing mechanism include snaps, buttons, or Velcro.

In some embodiments, an infant swaddle system includes two infant swaddle devices, each operable to be wrapped around each of the infant's arms, as illustrated in FIG. 7A. Each sleeve may include a tab with a securing mechanism for connecting the two infant swaddle devices together for storage.

FIG. 7B shows an infant's arm with the swaddle device 10 attached. This view illustrates the weighting pockets 12 and the splint pockets 16 from the front. In some examples, there may be a portion of extra fabric 30 at the top of the sleeve, near the shoulder, to be used to provide additional symmetry to the device and comfort and warmth for the infant, if needed. Referring again to FIG. 7B, the infant's elbow 28 is shown to be restricted in movement due to the splint 16 and weight 12 found in the sleeve.

Also provided herein is a method of reducing startle reflexes of an infant. The method may include wrapping a sleeve of an infant swaddle device around the infant's arm such that the infant's elbow is positioned within the sleeve. The inside facing portion of the sleeve is placed against the baby's arm (directly against the skin or against clothing) while the outside facing portion faces away from the arm. This orientation is maintained as the sleeve is wrapped around the infant's arm. In an example, the sleeve may be wrapped such that the sleeve and the infant's elbow are restrained from bending. In another example, the sleeve may be wrapped such that the sleeve and the infant's elbow are able to bend. The method further includes securing the attachment mechanism from the inside facing portion of the sleeve to the attachment mechanism of the outside facing portion. In some examples, this may include connecting the hook fasteners on the inside facing portion to the loop fasteners on the outside facing portion of the sleeve. The sleeve should be taught against the infant's arm, such that the baby's elbow is restrained from significant movement. In some examples, the sleeve allows the baby's elbow to slightly bend. The method may further include wrapping a second sleeve around the infant's other arm.

In various embodiments, the infant may be swaddled or unswaddled with a swaddle garment while wearing the swaddle device. If used under a swaddle garment, the swaddle device may make it less likely for the infant to be able to wriggle and move her arms too much because the arms are restrained snugly and independently of the baby's upper torso, thus reducing the likelihood of the swaddle garment gathering around her neck, mouth, and nose, which is a flaw in many current swaddle garments that could lead to potential suffocation.

When used with a swaddle garment, blanket, or suit the swaddle device may easily and effectively be able to keep the infant's arms in a downward position so that the infant's movements cannot loosen the binding and present a strangulation or suffocation hazard. Through the use of the swaddle device, parents may be able to use swaddle blankets without any worry of their infant getting their arms out or the swaddle loosening and finally unraveling, thus posing a safety hazard.

Although the invention described herein has been written about in detail, it should be appreciated that alterations, changes, and replacements may be made within the design without swaying from the original purpose and possibility of the invention in its most comprehensive arrangement. The illustrations provided are simply to be used as descriptors only and not restrictive in any manner, form, or purpose. Thus, other characterizing embodiments may be added to the design of the invention without straying from the fundamental characteristics mentioned herein. All such comparable embodiments and examples are within the spirit and scope of the invention discussed herein, are contemplated thereby, and proposed to be protected by the following claims.

What is claimed is:

1. An infant swaddle device comprising:
    a sleeve comprising:
    an inside facing portion;
    an outside facing portion;
    a first tapered end;
    a second tapered end; and
    multiple closable chambers,
    wherein the inside facing portion and the outside facing portion each comprise an attachment mechanism,
    wherein the multiple closable chambers are each operable to hold an adjustable weighting between the inside facing portion and the outside facing portion, the weighting comprising polyfill fiber or pellets, glass beads, bamboo beads, and/or sand,
    wherein the attachment mechanism on the outside facing portion comprises loop fasteners extending from the first tapered end of the sleeve to a point past the midpoint of the sleeve but not reaching a second end of the sleeve and covering the full width of the outside facing portion,
    wherein the attachment mechanism on the inside facing portion comprises hook fasteners extending from the second tapered end but not reaching the midpoint of the sleeve,
    wherein the inside facing portion further comprises one or more silicone dots extending from the second tapered end, opposite the hook fasteners,
    wherein the sleeve is operable to be wrapped around an infant's arm such that the infant's elbow is positioned within the sleeve, and
    wherein the sleeve reduces startle reflexes of the infant when wrapped around the infant's arm while the infant is sleeping.

2. The infant swaddle device of claim 1, wherein the sleeve is wrapped such that the sleeve and the infant's elbow are restrained from bending or the sleeve is wrapped such that the sleeve and the infant's elbow are able to bend.

3. The infant swaddle device of claim 1, wherein when the sleeve is wrapped around the infant's arm, the inside facing portion and the outside facing portion are reversibly attached together with the attachment mechanisms.

4. The infant swaddle device of claim 1, further comprising one or more splints operable to be received within the multiple closable chambers, wherein the one or more splints are operable to prevent the infant's elbow from bending when the sleeve is wrapped around the infant's arm.

5. The infant swaddle device of claim 4, wherein the one or more splints comprises plastic, metal, and/or cardboard.

6. The infant swaddle device of claim 1, wherein an upper edge of the sleeve is operable to rest just below the infant's armpit.

7. The infant swaddle device of claim 1, wherein a bottom edge of the sleeve is operable to rest just above the infant's wrist or just under the infant's elbow.

8. The infant swaddle device of claim 1, wherein the sleeve further comprises a tab extending from a longitudinal side of the sleeve near one end of the sleeve.

9. The infant swaddle device of claim 8, wherein the tab comprises a securing mechanism for connecting the sleeve to a second sleeve for storage.

10. An infant swaddle system comprising two infant swaddle devices, wherein each infant swaddle device comprises:
    a sleeve comprising:
    an inside facing portion;
    an outside facing portion;
    a first tapered end;
    a second tapered end; and
    multiple closable chambers,
    wherein the inside facing portion and the outside facing portion each comprise an attachment mechanism,
    wherein the multiple closable chambers are each operable to hold an adjustable weighting between the inside facing portion and the outside facing portion, the weighting comprising polyfill fiber or pellets, glass beads, bamboo beads, and/or sand,
    wherein the attachment mechanism on the outside facing portion comprises loop fasteners extending from the first tapered end of the sleeve to a point past the midpoint of the sleeve but not reaching a second end of the sleeve and covering the full width of the outside facing portion, wherein the attachment mechanism on the inside facing portion comprises hook fasteners extending from the second tapered end but not reaching the midpoint of the sleeve, wherein the inside facing portion further comprises one or more silicone dots extending from the second tapered end, opposite the hook fasteners, wherein the sleeve is operable to be wrapped around an infant's arm such that the infant's elbow is positioned within the sleeve, and wherein the sleeve reduces startle reflexes of the infant when wrapped around the infant's arm while the infant is sleeping.

11. The infant swaddle system of claim 10, wherein each sleeve further comprises a tab extending from a longitudinal side of the sleeve near one end of the sleeve, the tab comprising a securing mechanism for connecting the two infant swaddle devices together for storage.

12. A method of reducing startle reflexes of an infant, the method comprising:

wrapping a sleeve of an infant swaddle device around the infant's arm such that the infant's elbow is positioned within the sleeve, the sleeve comprising:

an inside facing portion;

an outside facing portion;

a first tapered end;

a second tapered end; and multiple closable chambers, wherein the inside facing portion and the outside facing portion each comprise an attachment mechanism, wherein the multiple closable chambers are each operable to hold an adjustable weighting between the inside facing portion and the outside facing portion, the weighting comprising polyfill fiber or pellets, glass beads, bamboo beads, and/or sand, wherein the attachment mechanism on the outside facing portion comprises loop fasteners extending from the first tapered end of the sleeve to a point past the midpoint of the sleeve but not reaching a second end of the sleeve and covering the full width of the outside facing portion, wherein the attachment mechanism on the inside facing portion comprises hook fasteners extending from the second tapered end but not reaching the midpoint of the sleeve, and wherein the inside facing portion further comprises one or more silicone dots extending from the second tapered end, opposite the hook fasteners.

13. The method of claim 12, wherein the infant is swaddled or unswaddled.

14. The method of claim 12, wherein the sleeve further comprises a tab with a securing mechanism.

* * * * *